United States Patent [19]

Ruddy et al.

[11] Patent Number: 5,585,108
[45] Date of Patent: Dec. 17, 1996

[54] FORMULATIONS OF ORAL GASTROINTESTINAL THERAPEUTIC AGENTS IN COMBINATION WITH PHARMACEUTICALLY ACCEPTABLE CLAYS

[75] Inventors: Stephen B. Ruddy, Schwenksville; W. Mark Eickhoff, Downingtown; Gary Liversidge, West Chester; Eugene R. Cooper, Berwyn, all of Pa.

[73] Assignee: Nanosystems L.L.C., Collegeville, Pa.

[21] Appl. No.: 366,518

[22] Filed: Dec. 30, 1994

[51] Int. Cl.⁶ .............................. A61K 9/02; A61K 9/16
[52] U.S. Cl. ..................... 424/434; 424/489; 424/501
[58] Field of Search ........................... 424/78.01, 434, 424/489, 501

[56] References Cited

U.S. PATENT DOCUMENTS

| | | |
|---|---|---|
| 4,010,252 | 3/1977 | Hewitt ........................ 424/66 |
| 4,107,288 | 8/1978 | Oppenheim et al. . |
| 4,501,726 | 2/1985 | Schroder et al. . |
| 4,801,608 | 1/1989 | Bos et al. ........................ 424/653 |
| 4,927,624 | 5/1990 | Bryant et al. ........................ 436/173 |
| 5,015,452 | 5/1991 | Matijevic . |
| 5,015,469 | 5/1991 | Yoneyama et al. ........................ 424/59 |
| 5,107,842 | 4/1992 | Levene et al. . |
| 5,118,528 | 6/1992 | Fessi et al. . |
| 5,145,684 | 9/1992 | Liversidge et al. . |

FOREIGN PATENT DOCUMENTS 5965016  4/1984  Japan .

*Primary Examiner*—Thurman K. Page
*Assistant Examiner*—J. Spear

[57] ABSTRACT

Nanoparticulate crystalline therapeutic substances formulated with stabilizers and pharmaceutically acceptable clays to enhance contact between the crystalline therapeutic substances and the gastrointestinal tract and to provide extended therapeutic effect.

4 Claims, No Drawings

FORMULATIONS OF ORAL GASTROINTESTINAL THERAPEUTIC AGENTS IN COMBINATION WITH PHARMACEUTICALLY ACCEPTABLE CLAYS

BACKGROUND OF THE INVENTION

1. Field of the Invention

This invention relates to formulations of gastrointestinal therapeutic agents in combination with pharmaceutically acceptable clays.

2. Reported Developments

In the delivery of certain slightly water-insoluble drugs intended to act by contact with the mucosal surface of the gastrointestinal tract (hereinafter sometimes referred to as GI tract) without substantial absorbance therethrough into the blood stream, the problem of insufficient adherence and dvelve time are often encountered. Drug, such as antacids, antimicrobial and antifungal agents tend to pass through the GI tract rapidly without providing sufficient local preventive/unactive effects.

Accordingly, there is a need to provide oral GI formulations that are safe, efficacious and have sufficient dvell or contact time with the GI mucosa. Such formulations should have excellent mucosal coating properties for both the upper and lower GI tract, i.e. it should have mucoadhesive or bioadhesive properties that enable the entire GI tract to be coated. Since the slightly watersoluble drugs do not by themselves possess such bioadhesive or mucoadhesive properties, the formulations containing them must provide the same.

The identification of surface active stabilizers with bioadhesive or mucoadhesive properties that enable coating of the entire GI tract with therapeutic agents has not been reported to date.

Bioadhesion is usually achieved by interaction of either a synthetic or natural polymeric substance with the mucosal membranes of the GI tract. Such technology has been employed to enhance drug delivery by decreasing the transit time of a drug substance in the GI tract and hence promote an opportunity for enhanced absorption. With regards to the development water-insoluble or poorly water-soluble drug formulations intended to coat the GI tract, it is important to identify mucosal adhesives that coat the GI surfaces and affect diseased or abnormal tissues. Highly charged carboxylated polyanions are good candidates for use as bioadhesives in the GI tract. See, for example: Park, K. and Robinson, J. R., Bioadhesion: Polymers and Platforms for Oral-Controlled Drug Delivery; Method to Study Bioadhesion. Int. J. Pharm., 19, 107 (1984). The formation of a bioadhesive bond between a polymeric substance and the mucosal lining of the GI tract can be visualized as a two step process, i.e., initial contact between the two surfaces and the formation of secondary bonds due to non-covalent interactions. Bioadhesives specific for the GI tract must interact with the mucus layer during attachment. Mucus, a general term for the heterogenous secretion found on the epithelial surfaces of the GI tract, is made of the following components: glycoprotein macromolecules, inorganic salts, proteins, lipids and mucopolysaccharides. These glycoproteins typically consist of a protein core with carbohydrate side chains. This forms a network of mucus that is a continuous layer covering the GI tract. From a bioadhesive perspective, mucus consists of highly hydrated, crosslinked linear, flexible yet random coiled glycoprotein molecules with a net negative charge.

Understanding the principles of bioadhesion is the basis for formulating an oral compositions for coating the GI tract. Bioadhesion accounts for the interaction between a biological surface and a biomaterial substance. As noted previously, bioadhesive agents are usually polymeric substances that adhere to tissues by ionic or covalent bonds or by physical attachment. Several theories of bioadhesion have been published including electronic, adsorption, wetting, diffusion and fracture theories. Bioadhesives bind to membrane surfaces and are retained for variable periods of time.

We have now discovered that certain therapeutic drugs in a combination with bioadhesive or mucoadhesive surfactants and pharmaceutically acceptable clays provide excellent coating on the GI tract for a prolonged period of time so that the therapeutic drugs are able to affect diseased conditions which may be present in the GI tract.

In accordance with the present invention, there is provided an orally/rectally administrable GI formulations containing an effective amount of a water-insoluble or poorly water-soluble therapeutic agent. There is further provided a method for affecting diseased conditions in the Gi tract comprising oral or rectal administration to a patient an effective amount of the above-identified formulation to prevent or cure such diseased conditions.

SUMMARY OF THE INVENTION

In accordance with the present invention there is provided an orally/rectally administrable therapeutic composition comprising:

- of from about 4 to about 45% w/v, and preferably of from about 5 to about 25% w/v, of an essentially water insoluble or poorly water-soluble particulate crystalline material having an effective average particle size of less than about 2,000 nm, more preferably an effective average particle size of less than about 1,000 nm, and most preferably an effective average particle size of less than about 400 nm;
- of from about 0.1% to about 10% w/v, and preferably of from about 1% to about 6% w/v of a bioadhesive or mucoadhesive surfactant stabilizer (hereinafter sometimes referred to as "primary stabilizer");
- of from about 0.1 to about 10% w/v and preferably of from about 0.5 to about 5, and most preferably of from about 1 to 2% of a pharmaceutically acceptable clay selected from the group consisting of montmorillonite, beidelite, nontronite, hectorite and saponite; and
- water to make 100% w/v.

Secondary stabilizers may also be used in the x-ray contrast formulation up to about 1% w/v, preferably up to about 0.2% w/v, and most preferably up to about 0.1% w/v. Secondary stabilizers include dioctylsulfosuccinate (DOSS) and sodium lauryl sulfate (SLS).

Other ingredients customarily used in oral pharmaceutical formulations may also be included, such as flavorants, colorants and preservatives to provide pharmaceutically acceptable and palatable formulations.

DETAILED DESCRIPTION OF THE INVENTION

The present invention is based on the discovery that particulate crystalline materials can be rendered mucoadhesive or bioadhesive in the gastrointestinal tract when the particulate crystalline material is combined with certain surface active agents in a suspension.

The invention can be practiced with a wide variety of crystalline materials that are water-insoluble or poorly soluble in water. As used herein "poorly soluble" means that the material has a solubility in aqueous medium of less than about 10 mg/ml, and preferably of less than about 1 mg/ml. Suitable drug substances for use in the present invention follow.

Drugs

Suitable drug substance can be selected from a variety of known classes of drugs including, for example, antacids, anti-inflammatory agents, antibiotics (including penicillins), antimycobacterial agents, antiviral agents, corticosteroids, parasympathomimetics, radio-pharmaceuticals, sympathomimetics, demulcents, emollients, gastrointestinal protectives and adsorbents, antifungals, H2-blocking agents, proton pump inhibitors, muscarinic antagonists, bismuth compounds, sucralfate, carbenoxolone, prostaglandins, digestants, bile acids, laxatives, antiparasitic agents, anthelmintics, antiprotozoal agents, antimicrobial agents, vitamins, immunologic agents, vaccines, anesthetics, lipid-regulating agents and bile acid sequestrants. Preferred drug substances include those intended for oral administration and rectal administration. A description of these classes of drugs and a listing of species within each class can be found in Martindale, The Extra Pharmacopoeia, Twenty-Ninth Edition, The Pharmaceutical Press, London, 1989, the disclosure of which is hereby incorporated by reference in its entirety. The drug substances are commercially available and/or can be prepared by techniques known in the art.

Bioadhesives/Mucoadhesives

The surfactants found to have bioadhesive or mucoadhesive properties include:

1) Poloxamers having an average molecular weight of from about 1,000 to 15,000 daltons;
2) Polyvinyl alcohol;
3) Polyvinyl pyrrolidone,
4) Hydroxypropyl methylcellulose; and
5) Polyoxyethylene sorbitan mono-oleate (Tween 80).

Poloxamers are polyethylene-polypropylene glycol block polymers containing ethylene oxide (PEO) and propylene oxide (PPO) moles according to the formula (PEO)a - (PPO)b - (PEO)c wherein a is 46, 52, 62, 75, 97, 98, 122 and 128;

b is 16, 30, 35, 39, 47, 54 and 67; and c is 46, 52, 62, 75, 97, 98, 122 and 128.

Table 1 shows the various poloxamers by manufacturer-designated number.

TABLE 1

Molecular Weights of Poloxamers

| Poloxamer No. | Pluronic | Av. Mol. Wt. | Av. Values a | b | c |
|---|---|---|---|---|---|
| 401 | | 4,400 | 6 | 67 | 6 |
| 402 | | 5,000 | 13 | 67 | 13 |
| 403 | | 5,750 | 21 | 67 | 21 |
| 407 | F127 | 12,000 | 98 | 67 | 98 |
| 331 | | 3,800 | 7 | 54 | 7 |
| 333 | | 4,950 | 20 | 54 | 20 |
| 334 | | 5,850 | 31 | 54 | 31 |
| 335 | | 6,000 | 38 | 54 | 38 |
| 338 | F108 | 15,000 | 128 | 54 | 128 |

TABLE 1-continued

Molecular Weights of Poloxamers

| Poloxamer No. | Pluronic | Av. Mol. Wt. | Av. Values a | b | c |
|---|---|---|---|---|---|
| 282 | | 3,650 | 10 | 47 | 10 |
| 284 | | 4,600 | 21 | 47 | 21 |
| 288 | F98 | 13,500 | 122 | 47 | 122 |
| 231 | | 2,750 | 6 | 39 | 6 |
| 234 | | 4,200 | 22 | 39 | 22 |
| 235 | | 4,600 | 27 | 39 | 27 |
| 237 | F87 | 7,700 | 62 | 39 | 62 |
| 238 | F88 | 10,800 | 97 | 39 | 97 |
| 212 | | 2,750 | 8 | 35 | 8 |
| 215 | | 4,150 | 24 | 35 | 24 |
| 217 | F77 | 6,600 | 52 | 35 | 52 |
| 181 | | 2,000 | 3 | 30 | 3 |
| 182 | | 2,500 | 8 | 30 | 8 |
| 183 | | 2,650 | 10 | 30 | 10 |
| 184 | | 2,900 | 13 | 30 | 13 |
| 185 | | 3,400 | 19 | 30 | 19 |
| 188 | F68 | 8,350 | 75 | 30 | 75 |
| 122 | | 1,630 | 5 | 21 | 5 |
| 123 | | 1,850 | 7 | 21 | 7 |
| 124 | | 2,200 | 11 | 21 | 11 |
| 101 | | 1,100 | 2 | 16 | 2 |
| 105 | | 1,900 | 11 | 16 | 11 |
| 108 | F38 | 5,000 | 46 | 16 | 46 |

Certain number of these surfactants are also known as Pluronic, which is a brand name of BASF Corporation.

Preferred surfactants for use in the present invention are:

Pluronic F127

Pluronic F108

Pluronic F98

Pluronic F87

Pluronic F88

Pluronic 77

Pluronic F68 and

Pluronic F38.

Method of Preparing the Radiopaque Particulates

The particulates were prepared by milling the large particles mixed with an appropriate surface active agent to obtain the desired particle size. Alternatively, the large particulates may be comminuted to the desired particle size and subsequently intimately mixed with the appropriate surface active agent. The milling technique is described in U.S. Pat. No. 5,145,684, which is incorporated herein by reference.

As used herein, particle size refers to a number average particle size as measured by conventional particle size measuring techniques well known to those skilled in the art, such as sedimentation field flow fractionation, photon correlation spectroscopy, or disk centrifugation. By "an effective average particle size of less than about 400 nm" for example, it is meant that at least 90% of the particles have a weight average particle size of less than about 400 nm when measured by the above-noted techniques. With reference to the effective average particle size, it is preferred that at least 95% and, more preferably, at least 99% of the particles have a particle size less than the effective average, e.g., 400 nm. In particularly preferred embodiments, essentially all of the particles have a size less than 400 nm.

The particles of this invention can be prepared in a method comprising the steps of dispersing a substance in a liquid dispersion medium and applying mechanical means in the presence of grinding media to reduce the particle size of the substance to an effective average particle size of less than about 400 nm. The particles are reduced in size in the presence of the surface active agent. Alternatively, the particles can be intimately mixed with a surface active agent after attrition.

A general procedure for preparing the particles of this invention is set forth below. The substance selected is obtained commercially and/or prepared by techniques known in the art in a conventional coarse form. It is preferred, but not essential, that the particle size of the coarse substance selected be less than about 100 μm as determined by sieve analysis. If the coarse particle size of the substance is greater than about 100 μm, then it is preferred that the particles of the substance be reduced in size to less than 100 μm using a conventional milling method such as airjet of fragmentation milling.

The mechanical means applied to reduce the particle size of the substance conveniently can take the form of a dispersion mill. Suitable dispersion mills include a ball mill, an attritor mill, a vibratory mill, and media mills such as a sand mill and a bead mill. A media mill is preferred due to the relatively shorter milling time required to provide the intended result, i.e., the desired reduction in particle size.

The grinding media for the particle size reduction step can be selected from rigid media preferably spherical or particulate in form having an average size less than about 3 mm and, more preferably, less than about 1 mm. Such media desirably can provide the particles of the invention with shorter processing times and impart less wear to the milling equipment. The selection of material for the grinding media is not believed to be critical. We have found that zirconium oxide, such as 95% ZrO stabilized with magnesia, zirconium silicate and glass grinding media provide particles having levels of contamination which are believed to be acceptable for the preparation of pharmaceutical compositions. However, other media, such as stainless steel, titania, alumina, and 95% ZrO stabilized with yttrium, are expected to be useful. Preferred media have a density greater than about 3 g/cm$^3$.

The attrition time can vary widely and depends primarily upon the particular mechanical means and processing conditions selected. For ball mills, processing times of up to five days or longer may be required. On the other hand, processing times of less than 1 day (residence times of one minute up to several hours) have provided the desired results using a high shear media mill.

The particles must be reduced in size at a temperature which does not significantly degrade the substance. Processing temperatures of less than about 30°–40° C. are ordinarily preferred. If desired, the processing equipment can be cooled with conventional cooling equipment. The method is conveniently carried out under conditions of ambient temperature and at processing pressures which are safe and effective for the milling process. For example, ambient processing pressures are typical of ball mills, attritor mills and vibratory mills. Processing pressures up to about 20 psi (1.4 kg/cm$^2$) are typical of media milling.

Particle size analysis was carried out using the Microtract Ultrafine Particle Analyzer. (Leeds and Northrup Co.; St. Petersburg, Fla.) Nanosuspension particle size was determined during the milling process and again immediately before the nanosuspensions were administered to rodents. Particle size was determined on the Coulter Model N4MD Submicron Particle Analyzer. (Coulter Corp.; Miami Lakes, Fla.).

FORMULATION EXAMPLES

The following formulation examples will further illustrate the present invention.

Example 1

| | |
|---|---|
| Sucralfate | 20 g |
| Pluronic F127 | 4.0 g |
| Benzoate Sodium | 0.2 g |
| Saccharin Sodium | 0.1 g |
| FD&C Red No. 40 | 0.03 g |
| Water, qs | 100 ml |

Example 2

| | |
|---|---|
| Carbenoxolone | 15 g |
| Pluronic F127 | 4.0 g |
| Benzoate Sodium | 0.2 g |
| Sorbate Potassium | 0.15 g |
| Saccharin Sodium | 0.1 g |
| FD&C Red No. 40 | 0.03 g |
| Water, qs | 100 ml |

Example 3

| | |
|---|---|
| Ursodeoxycholic Acid | 25 g |
| Pluronic F88 | 5.0 g |
| Benzoate Sodium | 0.2 g |
| Saccharin Sodium | 0.1 g |
| FD&C Red No. 3 | 0.03 g |
| Water, qs | 100 ml |

Example 4

| | |
|---|---|
| Cholic Acid | 19 g |
| Sucrose | 10 g |
| Pluronic F77 | 4.0 g |
| Dioctylsulfosuccinate | 0.1 g |
| Methylparabens | 0.2 g |
| Propylparabens | 0.07 g |
| FD&C Yellow No. 5 | 0.03 g |
| Water, qs | 100 ml |

Example 5

| | |
|---|---|
| Vitamin B | 15 g |
| Pluronic F127 | 5 g |
| Sorbitol | 5 g |
| Benzoate Sodium | 0.2 g |
| Water, qs | 100 ml |

Example 6

| | |
|---|---|
| Penicillin | 22 g |
| HPMC (2% = 100 cps) | 2 g |
| Steam sterilized by autoclaving at 120° C. for 21 minutes & 5 psig | 0.2 g |
| Water, qs | 100 ml |

Example 7

| | |
|---|---|
| Antibacterial | 20 g |
| Pluronic F127 | 4.0 g |
| Benzoate Sodium | 0.2 g |
| Sorbate Potassium | 0.15 g |
| Saccharin Sodium | 0.1 g |
| Water, qs | 100 ml |
| Hydrochloric Acid | adjust to pH 4.0 |

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An orally/rectally administrable therapeutic formulation comprising:
   of from about 4 to about 45% w/v of an essentially water-insoluble particulate drug having an effective average particle size of less than about 2,000 nm;
   of from about 0.1 to about 10% w/v of a bioadhesive surfactant stabilizer selected from the group consisting of: polyethylene-polypropylene glycol block polymers of the formula (i)
   (i) (polyethylene oxide)a-(polypropylene oxide)-(polyethylene oxide)c wherein
      a is 46, 52, 62, 75, 97, 98, 122 and 128;
      b is 16, 30, 35, 39, 47, 54 and 67; and
      c is 46, 52, 62, 75, 97, 98, 122 and 128;
   (ii) polyvinyl alcohol,
   (iii) polyvinyl pyrrolidone,
   (iv) hydroxypropyl methylcellulose, and
   (v) polyoxyethylene sorbitan mono-oleate;
   from about 0.1 to 10% w/v of a pharmaceutically acceptable clay selected from the group consisting of: montmorillonite, beidelite, nontronite, hectorite and saponite;
   from 0 to about 1% w/v of a secondary stabilizer selected from the group consisting of dioctylsulfosuccinate and sodium lauryl sulfate; and
   water to make 100% w/v.

2. The therapeutic formulation of claim 1 wherein said drug is selected from the group consisting of: antacids, anti-inflammatory agents, antibiotics, antimycobacterial agents, antiviral agents, corticosteroids, parasympathomimetics, radio-pharmaceuticals, sympathomimetics, demulcents, emollients, gastrointestinal protectives and adsorbents, antifungals, H2-blocking agents, proton pump inhibitors, muscarinic antagonists, bismuth compounds, sucralfate, carbenoxolone, prostaglandins, digestants, bile acids, laxatives, antiparasitic agents, anthelmintics, antiprotozoal agents, antimicrobial agents, vitamins, immunologic agents, vaccines, anesthetics, lipid-regulating agents and bile acid sequestrants.

3. The therapeutic formulation of claim 1 wherein said pharmaceutically acceptable clay is
   montmorillonite, having the formula $$M^+Al_{3-y}(FeMg)_y Si_4 O_{10}(OH)_2 \cdot nH_2O;$$

or beidelite, having the formula $$M^+(Al_2(Si_{4-x}Al_x)O_{10}(OH)_2 \cdot nH_2O;$$

or nontronite, having the formula $$M^+(Fe_2^{3+}(Si_{4-x}Al_x)O_{10}(OH)_2 \cdot nH_2O;$$

wherein $M^+$ is Na, Ca or Mg.

4. The therapeutic formulation of claim 1 wherein said pharmaceutically acceptable clay is
   saponite, having the formula $$M+(Mg_{3-y}(AlFe)_y Si_{4-x}Al_x)O_{10}(OH)_2 \cdot nH_2O;$$

or hectorite, having the formula $$M^+(Mg_{3-y}Li_y)Si_4 O_{10}(OH)_2 \cdot nH_2O;$$

wherein $M^+$ is Na, Ca or Mg.

* * * * *